United States Patent
Sebastian et al.

(10) Patent No.: US 9,604,169 B2
(45) Date of Patent: Mar. 28, 2017

(54) DISCRETE BYPASS PARTICLE CONCENTRATOR

(71) Applicant: MASSACHUSETTS INSTITUTE OF TECHNOLOGY, Cambridge, MA (US)

(72) Inventors: Thomas Sebastian, Waltham, MA (US); Timothy Stephens, West Chatham, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

(21) Appl. No.: 14/664,771

(22) Filed: Mar. 20, 2015

(65) Prior Publication Data

US 2015/0265956 A1    Sep. 24, 2015

Related U.S. Application Data (60) Provisional application No. 61/969,038, filed on Mar. 21, 2014.

(51) Int. Cl.
*B01D 45/08* (2006.01)
*G01N 1/40* (2006.01)
*G01N 15/00* (2006.01)

(52) U.S. Cl.
CPC ............ *B01D 45/08* (2013.01); *G01N 1/40* (2013.01); *G01N 1/4077* (2013.01); *G01N 2015/0046* (2013.01)

(58) Field of Classification Search
CPC .......... B01D 45/04; B01D 45/08; G01N 1/40; G01N 1/4077; G01N 2015/0046
USPC ................... 55/308, 319, 434, 442
See application file for complete search history.

(56) References Cited

U.S. PATENT DOCUMENTS

| | | | |
|---|---|---|---|
| 2,001,259 A * | 5/1935 | Lucke | B01D 45/12 55/423 |
| 3,725,271 A * | 4/1973 | Giannotti | B01D 45/16 159/13.1 |
| 4,744,958 A * | 5/1988 | Pircon | B01D 45/08 261/116 |
| 6,056,798 A * | 5/2000 | Cox | B01D 45/04 55/319 |
| 6,290,065 B1 | 9/2001 | Kenning et al. | |
| 6,698,592 B2 | 3/2004 | Kenning et al. | |
| 7,704,294 B2 * | 4/2010 | Ariessohn | G01N 1/2202 55/434 |
| 8,247,764 B2 | 8/2012 | Vidal-De-Miguel | |
| 2009/0007786 A1* | 1/2009 | Plamondon | B01D 45/04 95/267 |
| 2013/0312609 A1* | 11/2013 | van Vorselen | B01D 45/16 95/268 |

(Continued)

OTHER PUBLICATIONS

Notification Concerning Transmittal of Copy of International Preliminary Report on Patentability (Chapter I of the Patent Cooperation Treaty) dated Sep. 29, 2016, issued in International Application No. PCT/US2015/021819.

(Continued)

*Primary Examiner* — Jason M Greene
(74) *Attorney, Agent, or Firm* — Steptoe & Johnson LLP (57) ABSTRACT

A discrete bypass particle concentrator can significantly reduce surface fouling and manufacturing cost by including bypass stages after each of concentration stages.

8 Claims, 8 Drawing Sheets

(56) References Cited

U.S. PATENT DOCUMENTS

2016/0032798 A1* 2/2016 Herman ................ B01D 45/08
                                                                                                                                 95/268

OTHER PUBLICATIONS

International Search Report dated Jun. 18, 2015, issued in International Application No. PCT/US2015/021819.
Written Opinion of the International Searching Authority dated Jun. 18, 2015, issued in International Application No. PCT/US2015/021819.

* cited by examiner

FIG. 1

Figure 1:
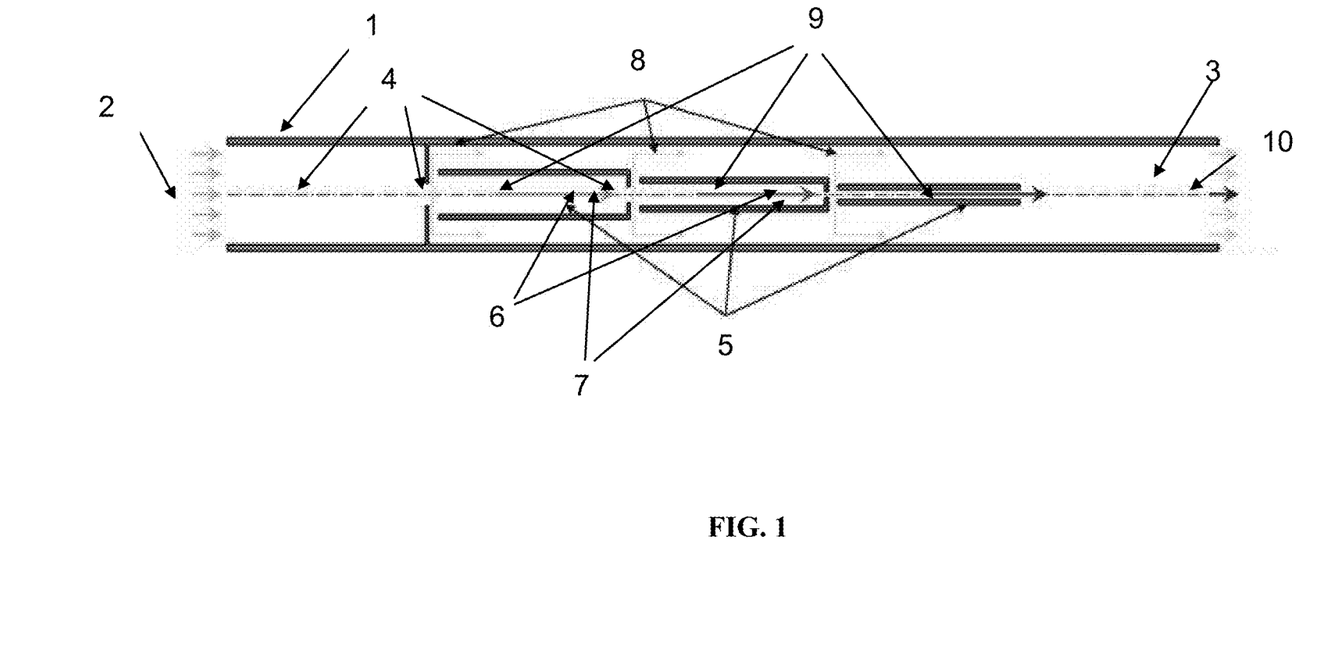
Figure 2:
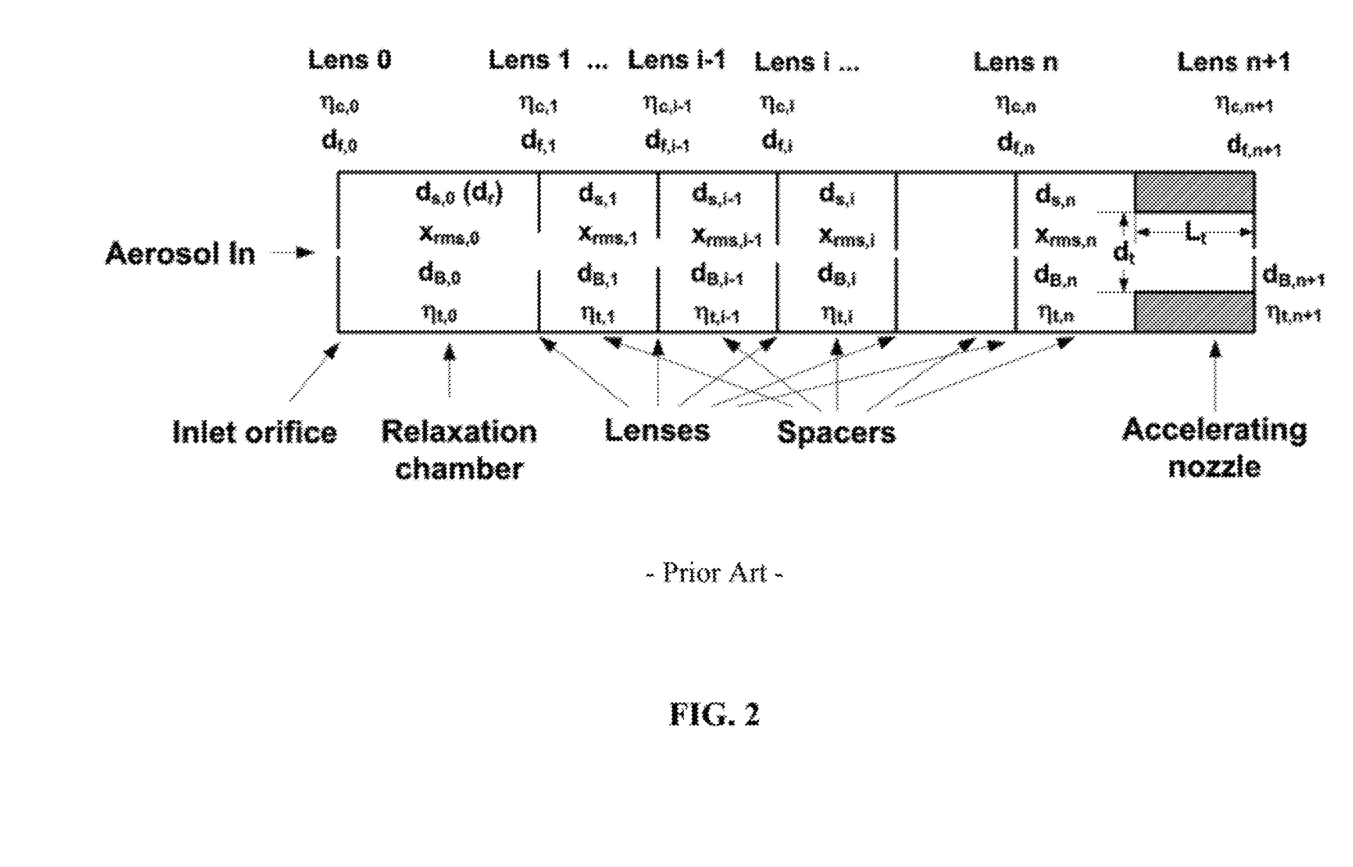
Figure 3:
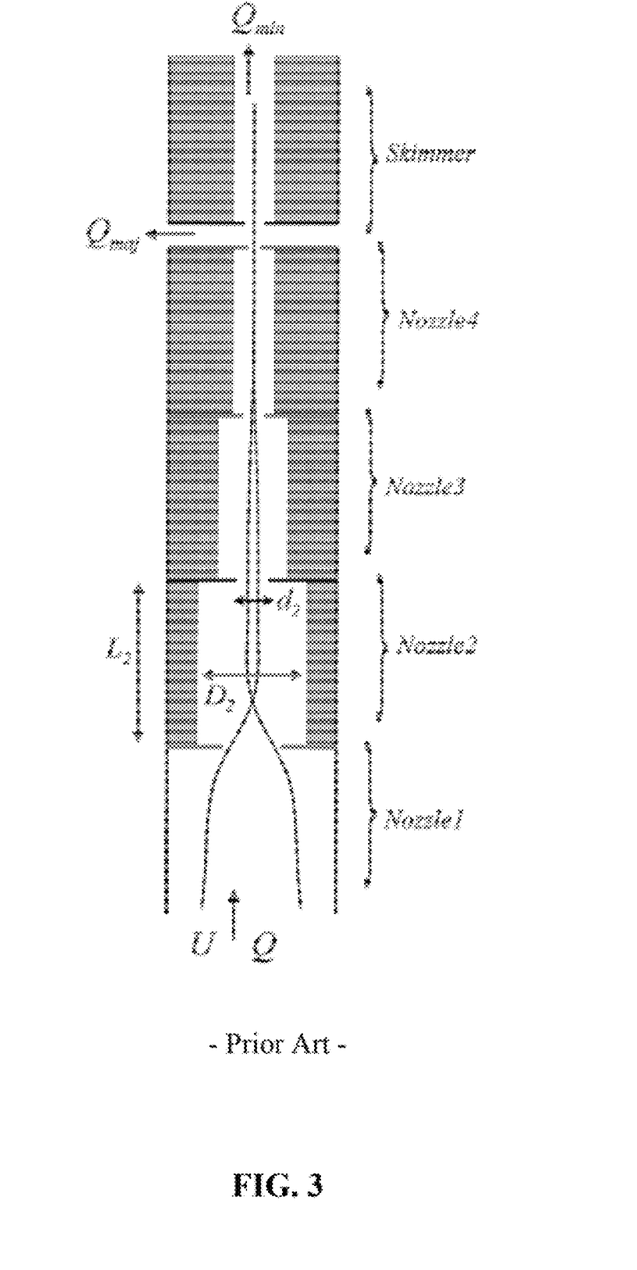

FIG. 2
- Prior Art -

- Prior Art -

… makes up the bulk of the flow, is skimmed off and the minor particle-laden flow, located on the centerline, continues through the final lens.

This effectively reduces the flow rate through the last concentration stage, thereby maintaining a laminar flow. However, the large pressure gradient in the region of the minor/major flow split may disrupt the particle beam and contribute to surface fouling, reducing performance over time. Physical tolerances in this area are also extremely tight, significantly increasing manufacturing costs. Explicit segregation of minor/major flows requires an additional sheath flow path downstream to prevent beam dispersion.

Figure 4:
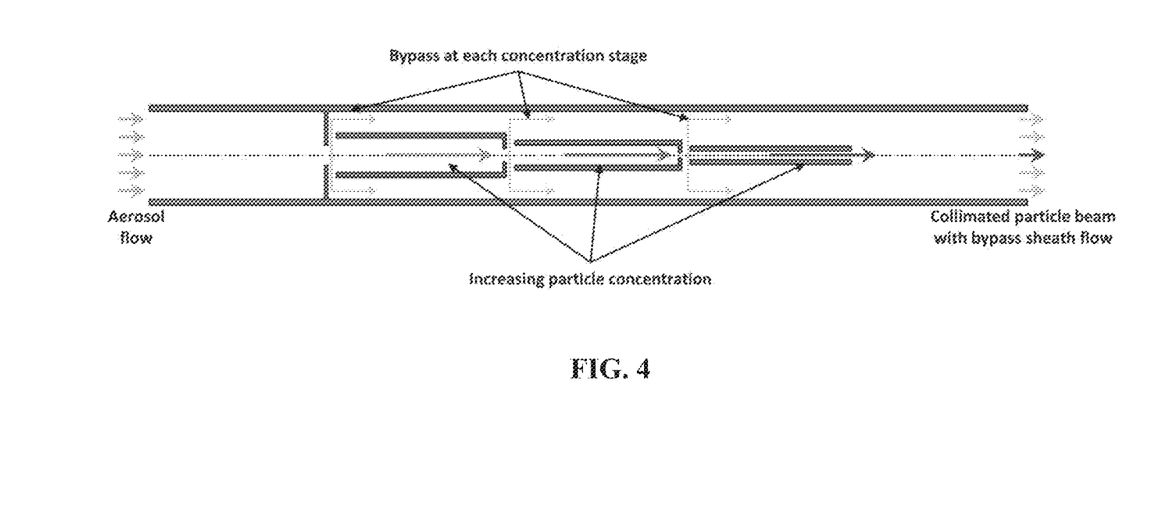
Figure 5:
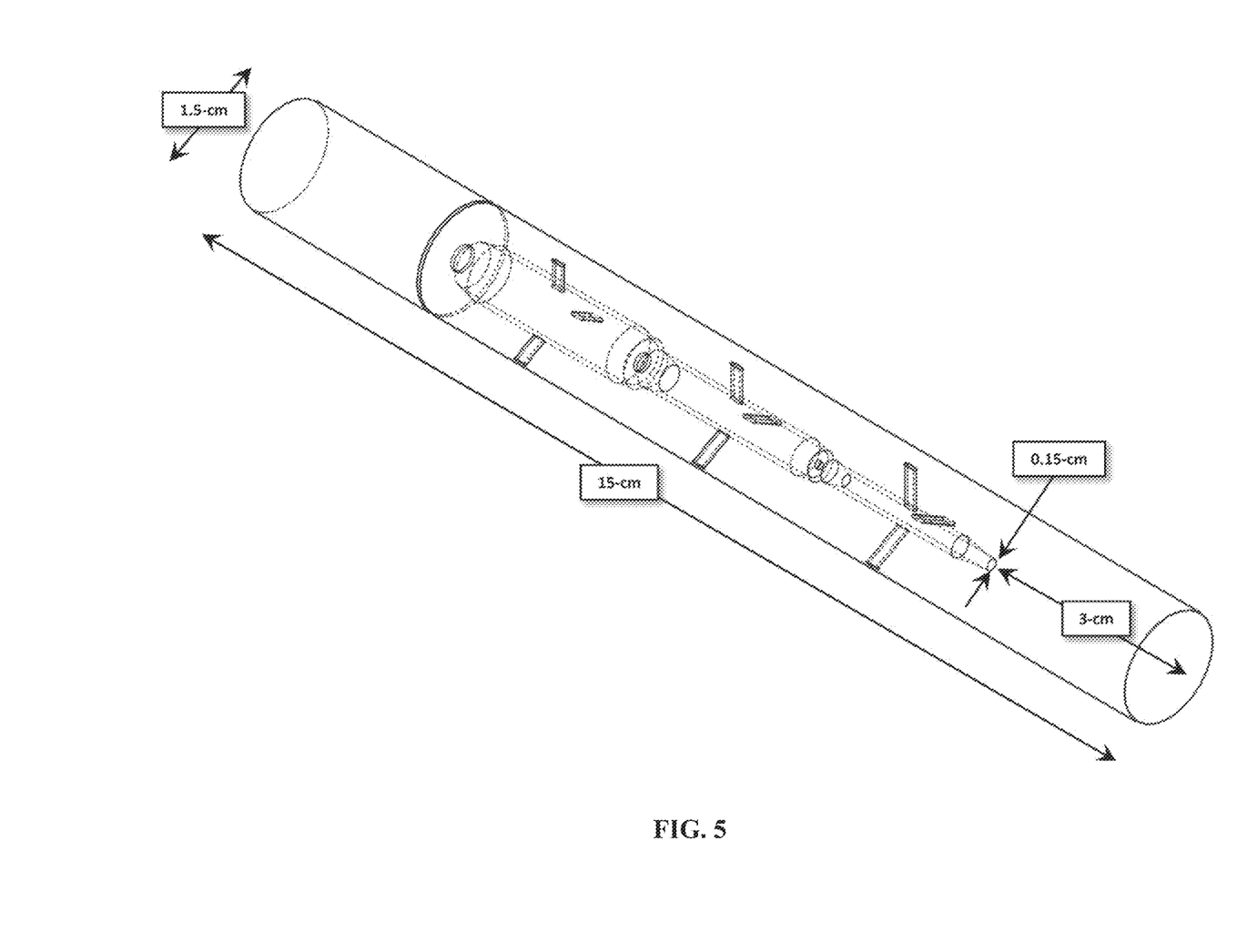
Figure 6:
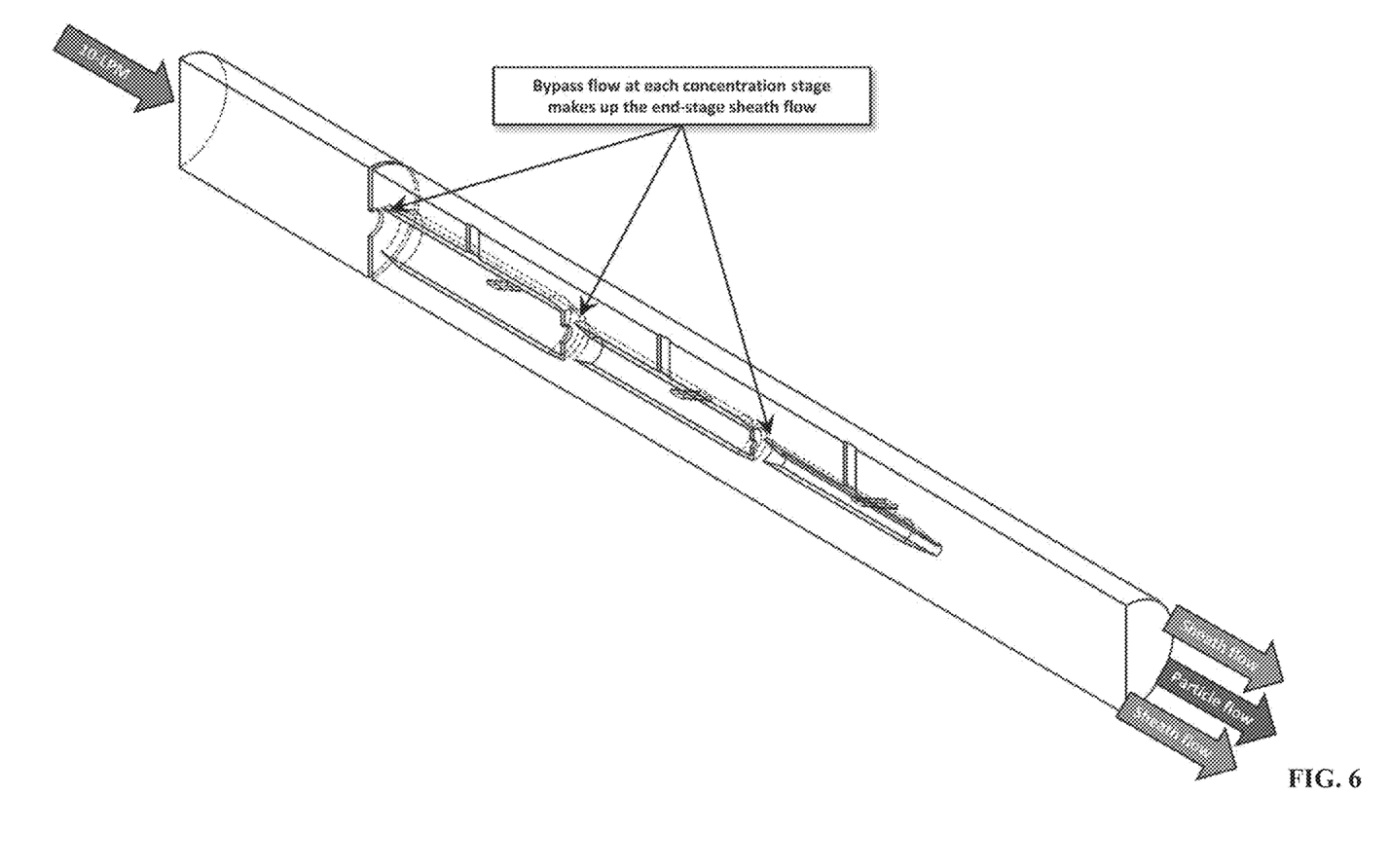
Figure 7:
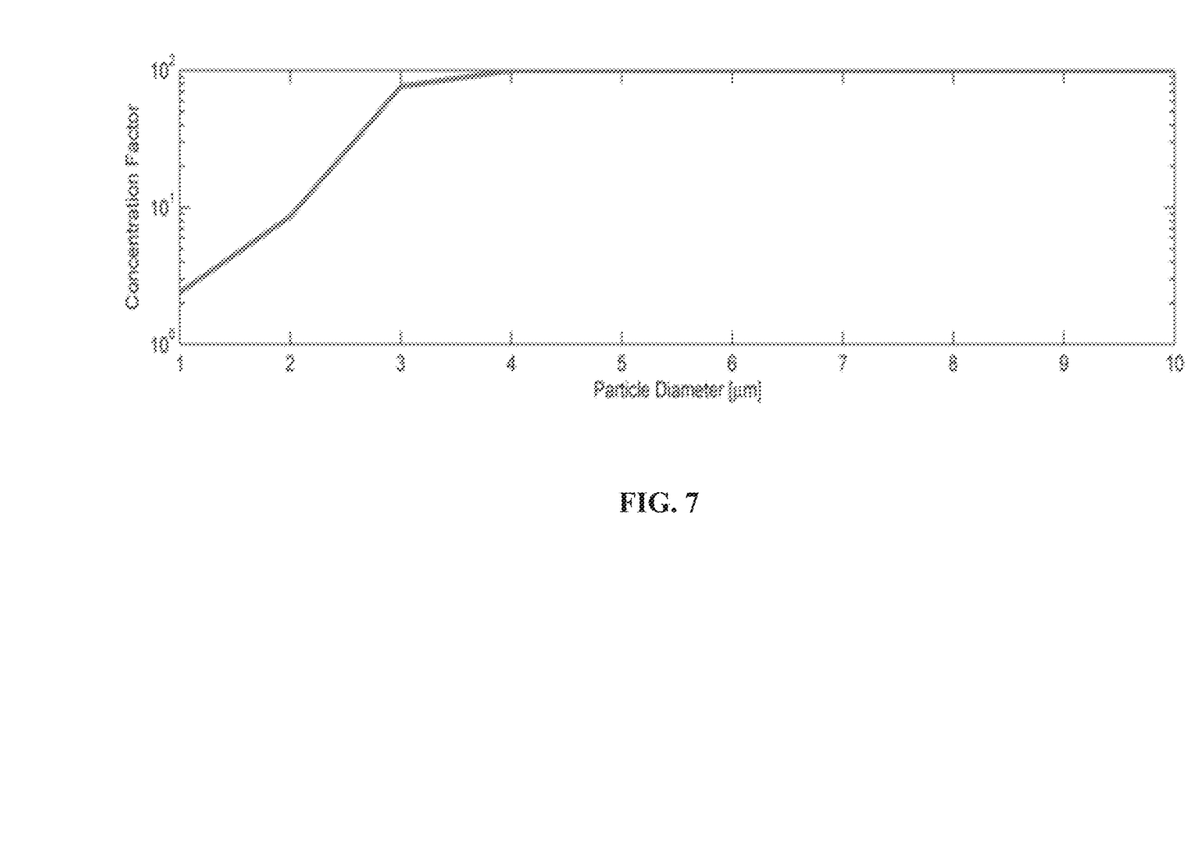
Figure 8:
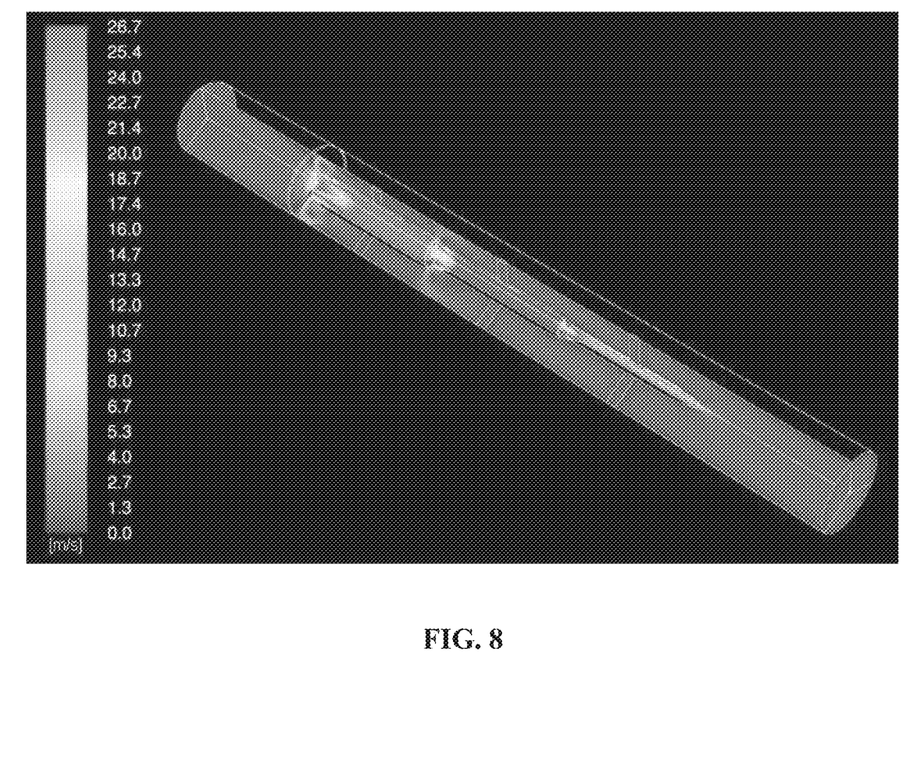

The discrete bypass concentrator introduces additional flow bypass stages after each of the concentrating lenses. A diagram illustrating this concept is shown in FIG. 4.

A discrete bypass concentrator can include a plurality of stages (i.e. lenses) where each stage includes an inlet, an outlet, and a flow channel, wherein the flow channel connects the inlet and the outlet, and the inside diameter of the flow channel is decreasing each stage, and a bypass between the outlet of a stage and the inlet of the following stage, wherein the flow that exists from a stage divides into a bypass flow that exits through the bypass and a particle flow that enters into the inlet of the flowing stage, wherein the main flow that exits from the last stage exits the device as a particle beam. The concentration stages can be positions in a series so that the main particle flow path would be straight to the exit. The size of the opening to a bypass flow is smaller than the size of the inlet flow, and the majority of the particles stay within the main flow. By splitting the flow at each stage, the ratio of particles to carrier gas at each concentration stage increases while the associated flow rate decreases. This permits more aggressive sizing of lenses and a possible reduction in the number of concentration stages. After the last concentration stage, the bypass flow from each stage forms a stabilizing, annular sheath flow around the tightly collimated particle beam, without the need for additional flow components. Distribution of the bypass flow also reduces the manufacturing tolerance requirements, yielding reduced fabrication costs.

The length of the device can vary. For example, it can be less than 1 m, less than 50 cm, less than 30 cm, or less than 15 cm. The diameter of the device can be less than 10 cm, less than 5 cm, less than 3 cm, or less than 1.5 cm. The length of each concentration stage can be less than 10 cm, less than 5 cm, less than 3 cm, or less than 1 cm. The size of the opening of the exit from the last stage can be less than 1 cm, less than 0.5 cm, less than 0.3 cm, or less than 0.15 cm.

The number of stages in the device can vary. For example, the device can have 2, 3, or more than 4 stages.

The size of the gap between the stages for the bypass flow can be between 0.1 mm and 1 cm. It can be less than 1 mm, less than 3 mm, less than 5 mm, or less than 1 cm. The flow rate can be between 0.5 L/min and 30 L/min. It can be less than 1 L/min, less than 5 L/min, less than less than 10 L/min, less than 20 L/min, or less than 30 L/min. The particle size can be between 0.25 μm and 25 μm. It can be less than 1 μm, less than 3 μm, less than 5 μm, less than 10 μm, less than 15 μm, or less than 25 μm.

An implementation of this approach has been designed to provide at least 40× concentration of 1-10 micron particles in a 10 L/min flow (FIGS. 5-6).

The resulting three-stage discrete bypass particle concentrator was simulated using computational fluid dynamics (CFD) and demonstrated a predicted 100× concentration of 4-10 micron particles, and high concentration factors for 1-3 micron particles (FIG. 7).

This performance is attributed to the flow balance between the particle and bypass flows (FIG. 8). Initial simulations indicate that the pressure drop generated by this concentrator is at least one order or magnitude lower than for comparable ADLs, resulting in decreased power requirements. Adjustments in lens shape and size, bypass gap length, and number of stages will allow for the successful application of this low-power approach to a wide range of flow rates and particle sizes.

Other embodiments are within the scope of the following claims.

What is claimed is:

1. A device for concentrating particles in a flow comprising:

a housing including a plurality of stages wherein each stage includes an inlet, an outlet, and a flow channel, wherein the flow channel includes an inside diameter and connects the inlet and the outlet, and the inside diameter of the flow channel is decreasing each subsequent stage; and a bypass between the outlet of a stage and the inlet of the following stage, wherein the flow that exits from a stage divides into a bypass flow within the housing that exits through the bypass and a particle flow that enters into the inlet of the flowing stage, wherein the particle flow that exits from the last stage exits the device as a particle beam, wherein the bypass flow includes less particles than the particle flow and forms an annular sheath flow around the particle beam.

2. The device of claim 1, wherein the plurality of stages is in a series with the inside diameter of the flow channel decreasing in each subsequent stages.

3. The device of claim 1, wherein the opening of the bypass is smaller than the opening of the inlet of the following stage.

4. The device of claim 1, wherein the particle beam and the bypass annular sheath flow are collimated.

5. The device of claim 1, wherein the size of flow channel and flow rate are configured for operation at Reynolds number of less than 2300.

6. The device of claim 1, wherein the size of flow channel and flow rate are configured for operation at Reynolds number of less than 1200.

7. The device of claim 1, wherein the length of the device is less than 20 cm.

8. The device of claim 1, wherein the size of a particle is between 1 μm and 10 μm.

* * * * *